(12) United States Patent
Albrecht et al.

(10) Patent No.: US 6,253,107 B1
(45) Date of Patent: Jun. 26, 2001

(54) CARDIAC PACING TO INDUCE HEART RATE VARIABILITY

(75) Inventors: Paul Albrecht, Bedford; Jeffrey M. Arnold, Wellesley, both of MA (US)

(73) Assignee: Cambridge Heart, Inc., Bedford, MA (US)

( * ) Notice: Subject to any disclaimer, the term of this patent is extended or adjusted under 35 U.S.C. 154(b) by 0 days.

(21) Appl. No.: 09/455,444

(22) Filed: Dec. 6, 1999

Related U.S. Application Data

(60) Provisional application No. 60/111,592, filed on Dec. 9, 1998.

(51) Int. Cl.$^7$ .................................................. A61N 1/362
(52) U.S. Cl. .............................................. 607/9; 600/513
(58) Field of Search .......................... 607/9, 10; 600/513

(56) References Cited

U.S. PATENT DOCUMENTS

| | | |
|---|---|---|
| 5,143,065 | 9/1992 | Adkins et al. . |
| 5,312,453 | 5/1994 | Shelton et al. . |
| 5,560,370 | 10/1996 | Verrier et al. . |
| 5,645,575 | 7/1997 | Stangl et al. . |
| 5,733,312 | 3/1998 | Schloss et al. . |
| 5,749,900 | 5/1998 | Schroeppel et al. . |

*Primary Examiner*—Scott M. Getzow
(74) *Attorney, Agent, or Firm*—Fish & Richardson P.C.

(57) ABSTRACT

Heart function is improved by inducing heart rate variability through cardiac pacing. Electrical pacing signals are generated and applyied to a heart to improve heart function. The pacing signals are controlled to vary a heart rate during periods of less than five minutes in duration to induce beneficial heart rate variability.

19 Claims, 3 Drawing Sheets

US 6,253,107 B1

CARDIAC PACING TO INDUCE HEART RATE VARIABILITY

CROSS-REFERENCE TO RELATED APPLICATIONS

This application claims priority from Provisional Application No. 60/111,592, which was filed Dec. 9, 1998, is titled Cardiac Pacing to Induce Heart Rate Variability, and is incorporated by reference.

BACKGROUND

Heart rate variability ("HRV") is known to be associated with a healthy heart. Numerous clinical studies have shown that patients with higher levels of heart rate variability have an increased chance of survival. Heart rate variability encompasses both long term HRV and short term HRV. Long term HRV is primarily the result of circadian rhythms and activity associated with sleep and awake cycles. Short term HRV is primarily the result of faster acting physiologic responses to respiration and blood pressure control. It has been demonstrated in clinical studies that both short term and long term HRV are related to likelihood of survival.

The beneficial effects of short term HRV are believed to be related to its modulating effect on the cardiac muscle cells and its ability to disrupt or diminish the evolution of dangerous patterns of electrical activity. One such important pattern is the pattern of electrical alternation in the action potential of the cardiac cells. It has been recognized that, in many patients who are at higher risk for serious cardiac arrhythmias, there may emerge a pattern of local or regional alternation in the action potential. This pattern of alternation is not always present, but often emerges under conditions where the patient's heart experiences an increased demand due to an increased level of physical or mental stress.

The pattern of alternation is referred to as electrical alternans. Electrical alternans can often be measured at the body surface as a subtle beat-to-beat change in the repeating pattern of an electrocardiogram (ECG) waveform. Alternans can be indicative of electrical instability of the heart and increased susceptibility to sudden cardiac death. Alternans results in an ABABAB ... pattern of variation of waveform shape between successive beats in an ECG waveform. An overview of electrical alternans is given by Rosenbaum, Albrecht and Cohen in "Predicting sudden cardiac death from T wave alternans of the surface electrocardiogram: promise and pitfalls.", *Journal of Cardiovascular Electrophysiology*, Nov., 1996, Vol. 7(11), pages 1095–1111, which is incorporated by reference.

SUMMARY

In one general aspect, the invention provides a method of improving heart function by inducing heart rate variability through cardiac pacing. The method includes generating electrical pacing signals and applying the electrical pacing signals to a heart to improve heart function. The pacing signals are controlled to vary a heart rate during periods of less than five minutes in duration to induce beneficial heart rate variability.

Implementations may include one or more of the following features. For example, the beneficial heart rate variability may be controlled to result in decreased likelihood of cardiac arrhythmia. For example, a measure of electrical stability of the heart related to likelihood of cardiac arrhythmia may be generated and used in generating the pacing signals. The measure of electrical stability may be, for example, a measure of electrical alternans or a measure of blood pressure alternans. Generating the pacing signals may include modifying the pacing signals in response to changes in the measure.

The pacing signals also may be controlled to mimic physiologic patterns of heart rate variability. Alternatively, the pacing signals may be controlled using a measure of a physiologic process, such as, for example, cardiac electrical activity, respiration, or blood pressure regulation. The pacing signals also may be controlled using a measure of the average heart rate.

The beneficial heart rate variability may result in improved left ventricular function.

The pacing signals also may be controlled to decrease a level of blood pressure alternans.

The pacing signals may be controlled to vary the heart rate by more than 2 percent. For example, the pacing signals may be controlled to vary the heart rate by more than 2 percent during a period of less than one minute in duration, less than 30 seconds in duration, or less than 10 seconds in duration.

In another general aspect, the invention features assessing cardiac electrical stability by generating a measure of cardiac electrical alternans, generating a measure of blood pressure alternans, and assessing cardiac electrical stability using both the measure of cardiac electrical alternans and the measure of blood pressure alternans.

Other features and advantages will be apparent from the following description, including the drawings, and from the claims.

DESCRIPTION

Figure 1:
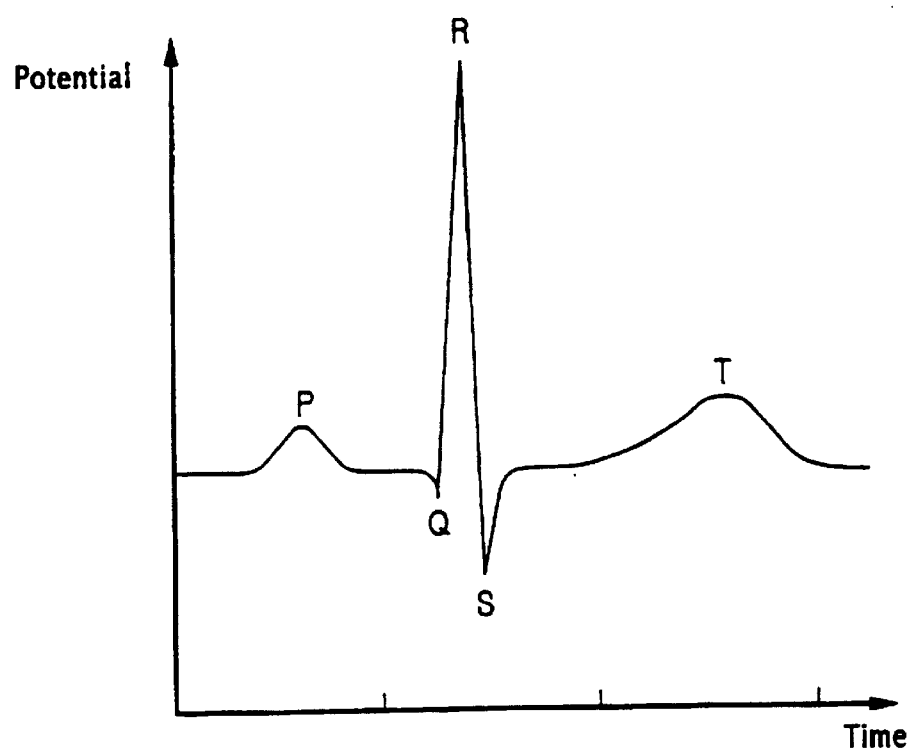
FIG. 1 is an ECG potential over a single beat.

Referring to FIG. 1, an ECG waveform for a single beat is typically referred to as a PQRST complex. Briefly, the P wave appears at initiation of the beat and corresponds to activity in the atria, while the QRST complex follows the P wave and corresponds to ventricular activity. The QRS component represents the electrical activation of the ventricles, while the T wave represents the electrical recovery thereof The ST segment is a relatively quiescent period. In humans, it has been found that the T wave is the best interval of the ECG complex for detecting alternans. That is, a level of alternation in the T waves of beats is recognized to be a good measure of a patient's level of electrical alternans.

Electrical alternans is brought about by an underlying pattern of alternation in the biochemical processes that drive the functioning of the cardiac muscle. As the level of alternation increases, it begins to have a measurable effect on the contraction of the muscle cells. This leads not only to electrical alternans, but also to an alternation in the beat-to-beat blood pressure waveform. The alternation in blood pressure is referred to as pulsus alternans. As with electrical alternans, it has been recognized that pulsus alternans may be a sign of diminished heart function.

The relationship between electrical alternans and pulsus alternans is examined by Clancy, Smith, and Cohen in "A simple electrical-mechanical model of the heart applied to the study of electrical-mechanical alternans.", *IEEE Transactions on Biomedical Engineering,* June, 1991, Vol. 38(6), pages 551–60, which is incorporated by reference. That paper noted evidence showing that a subtle alternation in the surface ECG (electrical alternans) may be correlated with the susceptibility to ventricular fibrillation, and offered evidence that a mechanical alternation in the heart beat (mechanical alternans) generally accompanies electrical alternans. The paper indicated that there exists a regime of combined electrical-mechanical alternans during the transition from a normal rhythm towards a fibrillatory rhythm, that the detected degree of alternation is correlated with the relative instability of the rhythm, and that the electrical and mechanical alternans may result from a dispersion in local electrical properties leading to a spatial-temporal alternation in the electrical conduction process.

Figure 2:
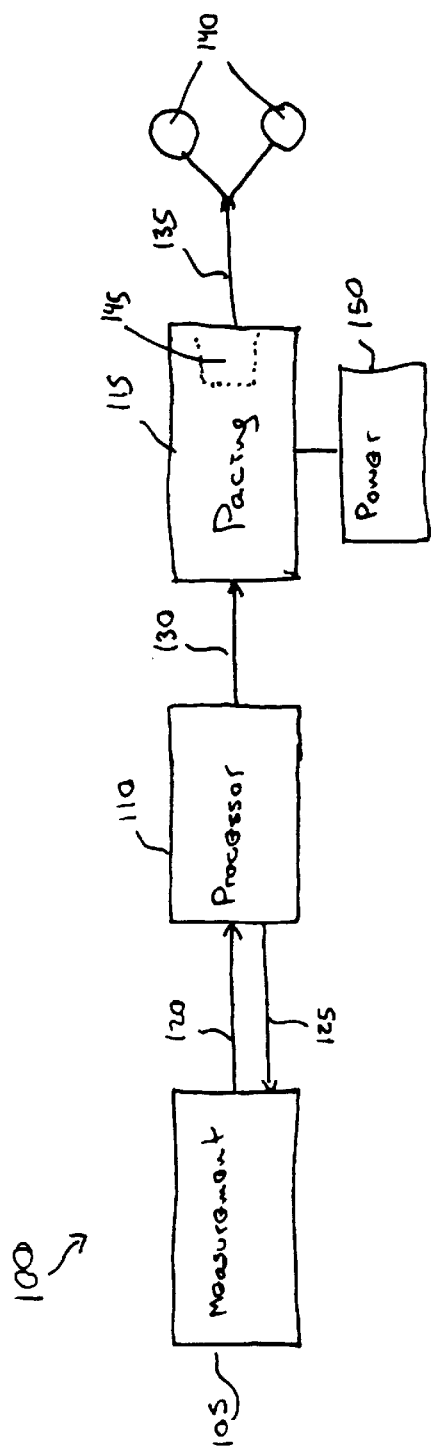
FIG. 2 is a block diagram of an implantable pacing system for inducing beneficial heart rate variability.

Referring to FIG. 2, an implantable pacing system 100 for inducing heart rate variability includes a measurement subsystem 105, a processor 110, and a pacing subsystem 115. The measurement subsystem 105 produces signals 120 related to cardiac and other processes of a patient in which the system 100 is implanted and provides the signals to the processor 110.

The processor 110 processes the signals 120 from the measurement subsystem 105 to produce control signals 125 that the processor uses to control the measurement subsystem 105 and control signals 130 that the processor uses to control the pacing subsystem 115. In general, and as discussed in more detail below, the processor produces the control signals 130 to induce beneficial heart rate variability in the patient.

The pacing subsystem 115 responds to the control signals 130 by generating pacing signals 135 and applying those signals to the patient's heart. To this end, the pacing subsystem 135 includes two or more electrodes 140 connected to a pacing circuit 145 and positioned to apply the pacing signals 135 to the patient's heart. The pacing subsystem 115 also includes a power supply 150, such as a battery, that supplies the power needed to generate the pacing signals.

Figure 3:
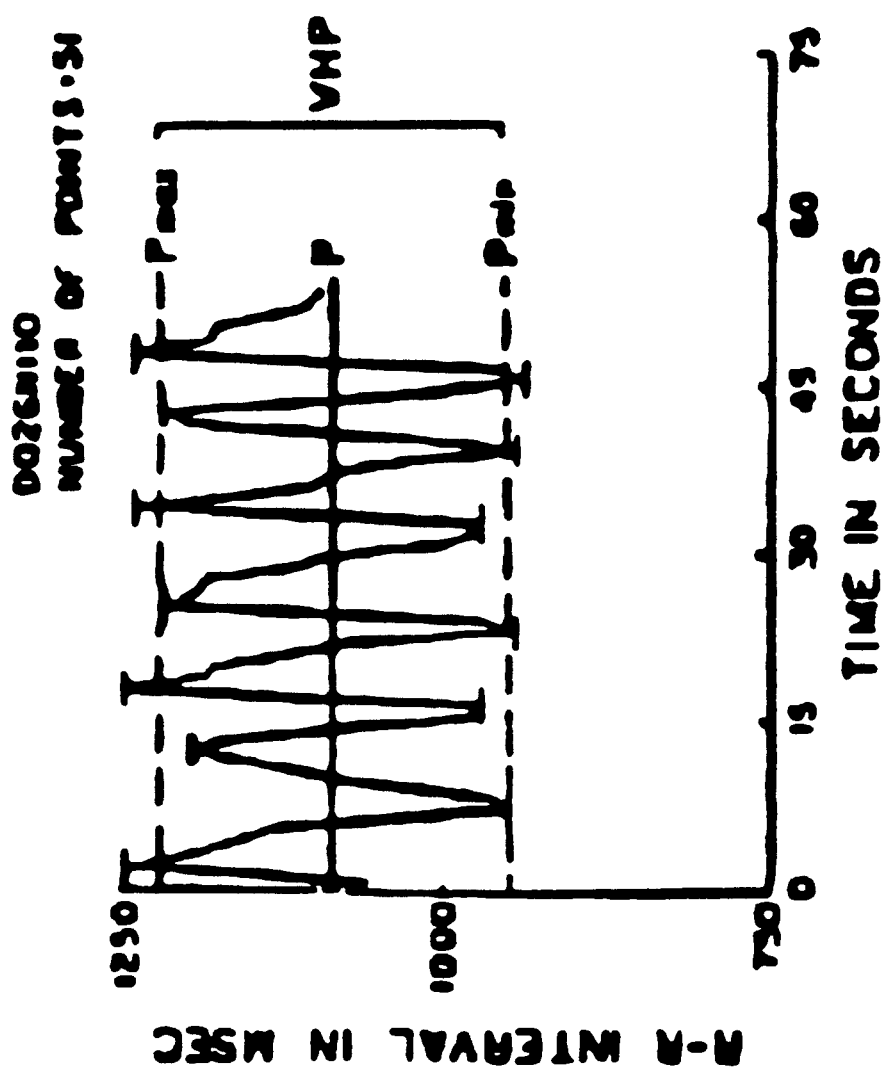
FIG. 3 is a graph of a heart rate variability pattern produced in a healthy patient by respiration.

Thus, the system generates electrical pacing signals and controls the signals to vary the patient's heart rate so as to induce beneficial heart rate variability. For example, the system may generate pacing signals that cause heart rate variability corresponding to that due to respiration in a healthy patient. Such variability is illustrated in FIG. 3. The variability illustrated in FIG. 3, referred to as the variation in heart period ("VHP") is calculated as the difference between the maximum and minimum RR intervals that occur during each breath.

As shown, the pattern extends over a period of approximately one minute and varies the heart period between about 0.95 seconds and 1.25 seconds, or by about 32%, where the percentage difference is determined from the difference between the largest and smallest RR intervals divided by the smallest RR interval. The system 100 may be configured to produce pulses having a similar pattern of durations. Other suitable patterns may vary the heart rate by as little as a few percent or as much as 30% or more during periods ranging from a few seconds to five minutes. As an alternative to the pseudo-periodic variability pattern illustrated in FIG. 4, the system could employ a more complex pattern of variability or a random pattern of variability, so long as the variability is controlled to produce a beneficial effect.

Figure 4:
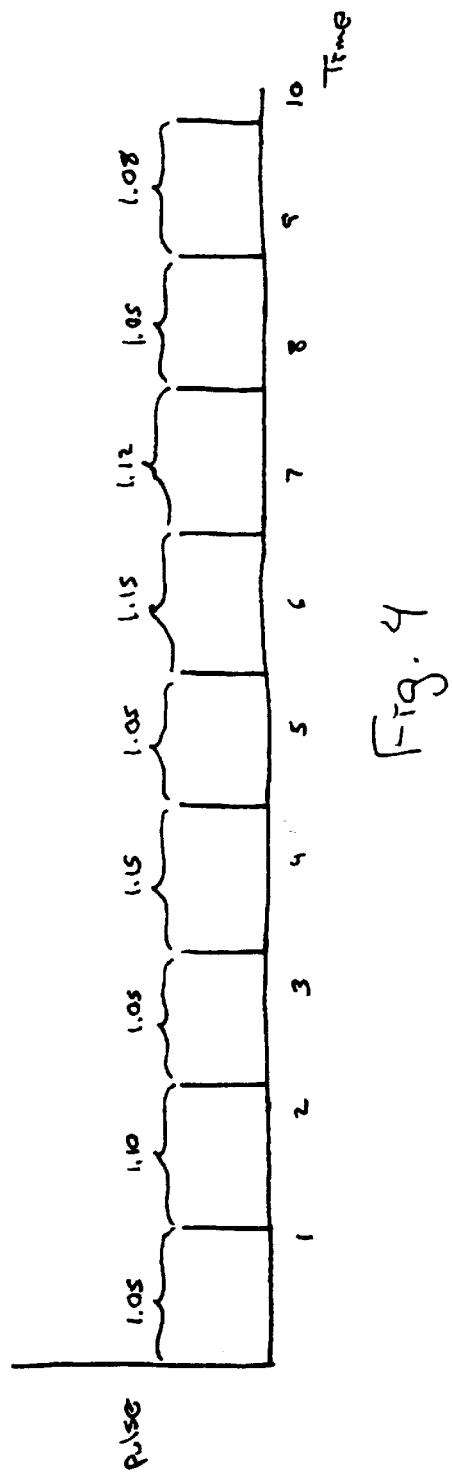
FIG. 4 is a timing chart showing timing of pacing pulses generated by the system of FIG. 2.

FIG. 4. shows the timing of pacing pulses generated by the system 100 over a 10 second interval. As shown, the pulses vary the heart period between about 1.05 and 1.15 seconds, or by about 9.5%. The timing chart of FIG. 4 illustrates each pacing pulse as a single, square pulse. The pulses are illustrated in this manner for the sole purpose of illustrating the gross timing of the pulses. It should be recognized that the pacing subsystem 115 will likely produce substantially more complex pulses for application to the patient's heart.

The system may be configured to induce the heart rate variability to decrease the chance of cardiac arrhythmia. To this end, the measurement subsystem 105 may be configured to generate a measure of electrical stability of the heart. As noted above, the processor 110 uses the measurement produced by the measurement subsystem 105 in generating the pacing signals.

A measure of electrical alternans is one such measure of electrical stability. Alternans can be indicative of electrical instability of the heart and increased susceptibility to sudden cardiac death. Alternans results in an ABABAB . . . pattern of variation of waveform shape between successive beats in an ECG waveform. The level of cardiac stability is characteristic of an individual's cardiac electrical stability.

Referring again to FIG. 1, the amplitude of an ECG waveform typically is measured using an isoelectric point as the zero voltage reference. The isoelectric point is measured during the PQ interval between the P wave and QRS complex. The PQ interval is a good approximation to a zero ECG level because there is no major electrical activity in the heart at that time. It is important to note that the ECG waveform has DC content and that the zero ECG level does not necessarily correspond to zero volts. Thus, any high pass filtering of the waveform will offset the isoelectric point.

While an ECG waveform typically has a QRS amplitude measured in millivolts, an alternans pattern of variation with an amplitude on the order of a microvolt may be clinically significant. Accordingly, the alternans pattern may be too small to be detected by visual inspection of the electrocardiogram and often must be detected and quantified electronically. Such electronic detection and quantification of the alternans pattern is further complicated by the presence of noise in the ECG waveforms, as the noise may result in beat-to-beat variations in the ECG waveforms that have a larger magnitude than the alternans pattern of variation. The electrical pattern of the PQRST measured by an implantable pacing device will have different relative amplitudes and shapes depending on the electrode locations used by the device. The electrodes may include individual leads or they may be integrated into the case of the pacing device, the pacing leads, or other physiologic signal sensors.

Techniques for detecting and assessing electrical alternans are described in U.S. Pat. Nos. 5,713,367, 5,704,365 and 5,724,984, and U.S. application Ser. No. 08/856,990, all of which are incorporated by reference.

Another suitable measure related to ventricular function and also to susceptibility to cardiac arrhythmia is a measure of pulsus alternans. As described above, pulsus alternans is an alternation in the beat-to-beat blood pressure waves. Accordingly, the measurement subsystem 105 may include a blood pressure sensor for use in detecting pulsus alternans.

Susceptibility to cardiac arrhythmia also may be assessed by generating a measure of cardiac electrical alternans, generating a measure of blood pressure alternans, and assessing cardiac electrical stability using both the measure of cardiac electrical alternans and the measure of blood pressure alternans.

The system may be configured to control the pacing signals to mimic naturally occurring heart rate variability, and may initiate the pacing signals in response to sensor signals indicative of electrical instability. The system may be configured to modify the pacing signals in response to changes in the measure of electrical stability.

The system also may control the pacing signals using a measure of a naturally occurring physiologic process. For example, the system could control the pacing signals based on respiration levels. Similarly, the system could control the pacing signals to regulate blood pressure. The beneficial heart rate variability may result in improved left ventricular function. The pacing signals also may be controlled to decrease a level of blood pressure alternans.

Other embodiments are within the scope of the following claims.

What is claimed is:

1. A method of improving heart function, the method comprising:
    generating electrical pacing signals, the pacing signals being controlled to vary a heart rate during periods of less than five minutes in duration to induce beneficial heart rate variability; and
    applying the electrical pacing signals to a heart to improve heart function.

2. The method of claim 1, wherein the beneficial heart rate variability results in decreased likelihood of cardiac arrhythmia.

3. The method of claim 2, further comprising generating a measure of electrical stability of the heart related to likelihood of cardiac arrhythmia and generating the pacing signals using the measure.

4. The method of claim 3, wherein the measure of electrical stability comprises a measure of electrical alternans.

5. The method of claim 3, wherein the measure of electrical stability includes a measure of blood pressure alternans.

6. The method of claim 3, wherein generating the pacing signals comprises modifying the pacing signals in response to changes in the measure.

7. The method of claim 1, wherein generating the pacing signals comprises controlling the pacing signals to mimic physiologic patterns of heart rate variability.

8. The method of claim 1, wherein generating the pacing signals comprises controlling the pacing signals using a measure of a physiologic process.

9. The method of claim 8, wherein the physiologic process comprises cardiac electrical activity.

10. The method of claim 8, wherein the physiologic process comprises respiration.

11. The method of claim 8, wherein the physiologic process comprises blood pressure regulation.

12. The method of claim 1, wherein generating the pacing signals comprises controlling the pacing signals using a measure of the average heart rate.

13. The method of claim 1, wherein the beneficial heart rate variability results in improved left ventricular function.

14. The method of claim 1, wherein generating the pacing signals comprises controlling the pacing signals to decrease a level of blood pressure alternans.

15. The method of claim 1, further comprising controlling the pacing signals to vary the heart rate by more than 2 percent.

16. The method of claim 15, further comprising controlling the pacing signals to vary the heart rate by more than 2 percent during a period of less than one minute in duration.

17. The method of claim 16, further comprising controlling the pacing signals to vary the heart rate by more than 2 percent during a period of less than 30 seconds in duration.

18. The method of claim 16, further comprising controlling the pacing signals to vary the heart rate by more than 2 percent during a period of less than 10 seconds in duration.

19. A method of assessing cardiac electrical stability, the method comprising:
    generating a measure of cardiac electrical alternans;
    generating a measure of blood pressure alternans; and
    assessing cardiac electrical stability using both the measure of cardiac electrical alternans and the measure of blood pressure alternans.

* * * * *